United States Patent [19]
Lichtstein et al.

[11] Patent Number: 5,874,423
[45] Date of Patent: Feb. 23, 1999

[54] DIGITALIS-LIKE COMPOUNDS

[75] Inventors: David Lichtstein; Joseph Deutsch; Irit Gati, all of Jerusalem, Israel

[73] Assignee: Yissum Research Development Co. of the Hebrew University of Jerusalem, Jerusalem, Israel

[21] Appl. No.: 713,151

[22] Filed: Sep. 12, 1996

Related U.S. Application Data

[63] Continuation-in-part of Ser. No. 397,160, Apr. 10, 1995, abandoned, filed as PCT/US93/08393 Sep. 8, 1993.

[30] Foreign Application Priority Data

Sep. 10, 1992 [IL] Israel ........................................ 103132

[51] Int. Cl.⁶ .......................... A01N 45/00; A01N 43/04; A61K 38/00; A61K 35/12
[52] U.S. Cl. .............................. 514/169; 514/21; 514/34; 540/72; 536/5; 424/520
[58] Field of Search ................................ 514/34, 21, 169; 540/72; 536/5; 424/520

[56] References Cited

U.S. PATENT DOCUMENTS

| | | | |
|---|---|---|---|
| 3,791,932 | 2/1974 | Schuurs et al. | 195/103.5 R |
| 3,839,153 | 10/1974 | Schuurs et al. | 195/103.5 R |
| 3,850,578 | 11/1974 | McConnell | 23/230 B |
| 3,850,752 | 11/1974 | Schuurs et al. | 195/103.5 R |
| 3,853,987 | 12/1974 | Dreyer | 424/1 |
| 3,867,517 | 2/1975 | Ling | 424/1 |
| 3,879,262 | 4/1975 | Schuurs et al. | 195/99 |
| 3,901,654 | 8/1975 | Gross | 23/230 B |
| 3,935,074 | 1/1976 | Rubenstein et al. | 195/103.5 R |
| 3,984,533 | 10/1976 | Uzgiris | 23/230 B |
| 3,996,345 | 12/1976 | Ullman et al. | 23/230 B |
| 4,034,074 | 7/1977 | Miles | 424/1 |
| 4,098,876 | 7/1978 | Piasio et al. | 424/1 |
| 4,380,624 | 4/1983 | Wiesner et al. | 536/5 |
| 4,780,314 | 10/1988 | Graves | 424/95 |
| 4,879,219 | 11/1989 | Wands et al. | 435/7 |
| 5,011,771 | 4/1991 | Bellet et al. | 435/7.94 |
| 5,281,521 | 1/1994 | Trojanowski et al. | 435/7.5 |

OTHER PUBLICATIONS

Gupta et al., "Cellular Basis for the Species Differences in Sensitivity to Cardiac Gycosides (Digitalis)", *J. Cell. Physiol.* 127(2) : 197–206 (1986).

Clarkson and de Wardener, "Observations on a low molecular weight natriuretic and Na–K–ATpase inhibitory material in urine" *Clin. and Exper.—Theory and Practice*, A7(5&6), pp. 673–683 (1985).

Akagawa et al., "Partial purification and properties of the inhibitors of Na, K–ATPase and Ouabain–binding . . . " *J. Neurochem.* 42:775–780 (1984).

Bidard et al., "A search for an 'ouabain–like' substance from the electric organ of *electrophorus electricus . . . " Biochim. Biphys. Acta* 769:245–252 (1984).

Cloix et al., "An endogenous digitalis–like compound extracted from human urine: biochemical and chemical studies" *Can. J. Physiol. Pharmacol.*, 65:1522–1527 (1987).

Cotlier, "The Lens" in *Adler's Physiology of the Eye*, pp. 277–303, ed. R.A. Moses, The C.V. Mosby Company, St. Louis (1981).

Dasgupta et al., "Two novel endogenous digoxin–like immunoreactive substances isolated from human plasma ultrafiltrate" *Biochem. Biophys. Res. Commun.*, 148:623–628 (1987).

De Pover et al., "Water versus acetone–HCl extraction of digitalis–like factor from guinea–pig heart" *Biochem. Pharmacol.*, 31:267–271 (1982).

De Wardener and Clarkson, "Concept of natriuretic hormone" *Physiological Reviews*, 65:658–759 (1985).

Fagoo et al., "Evidence that mammalian lignans show endogenous digitalis–like activities" *Biochem. Biophys. Res. Commun.* 134:1064–1070 (1986).

Flier et al., "Widespread occurrence in frogs and toads of skin compounds interacting with the Ouabain . . . " *Science*, 208:503–505 (1980).

Fukui et al., "A possible cataractogenic factor in the nakano mouse lens" *Exp. Eye Res.*, 26:1–9 (1978).

(List continued on next page.)

Primary Examiner—Sandra E. Saucier
Attorney, Agent, or Firm—Kohn & Associates

[57] ABSTRACT

A human cataractous lens nuclei methanolic extract characterized in that it comprises substances having a molecular weight lower than 3000 daltons, inhibiting ATP hydrolysis by $Na^+,K^+$-ATPase having affinity to the ouabain binding site on the enzyme and cross-reacting with an antibody directed against digoxin. Compounds of the general formula are disclosed:

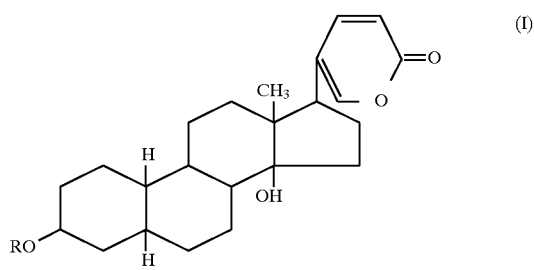

(I)

or of the general formula:

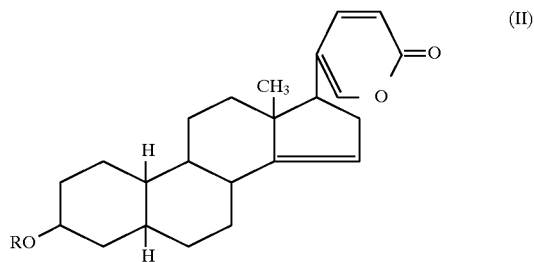

(II)

in which R is hydrogen, an amino acid, a di- or tripeptide or a mono-, di- or trisaccharide. Pharmaceutical preparations and methods of using the compounds are also disclosed.

9 Claims, 4 Drawing Sheets

OTHER PUBLICATIONS

Goto et al., "Isolation of urinary digitalis–like factor indistinguishable from digoxin" *Biochem. Biophys. Res. Commun.,* 173:1093–1101 (1990).

Gruber et al., "Endogenous digitalis–like substance in plasma of volume–expanded dogs" *Nature,* 237:743–745 (1980).

Haber and Haupert, "The search for a hypothalamic Na , K ATPase Inhibitor" *Hypertension,* 9:315–324 (1987).

Halperin et al., "Ouabain–like activity in human cerebrospinal fluid" *Proc. Natl. Acad. Sci. USA,* 80:6101–6104 (1983).

Hamlyn et al., "Identification and characterization of a ouabain–like compound from human plasma" *Proc. Natl. Acad. Sci. USA,* 88:6257–6263 (1991).

Haupert and Sancho, "Sodium transport inhibitor from bovine hypothalamus" *Proc. Natl. Acad. Sci. USA,* 76:4658–4660 (1979).

Itawa and Kinoshita, "Mechanism of development of hereditary cataract in mice" *Invest. Ophthalmol.,* 10:504–512 (1971).

Kamei and Sakai, "Characterization of peptide inducing cataractogenesis in lens of hereditary cataractous rat (ICR/f Rat)" Abstract only.

Kelly et al., "Identification of NaK–ATPase inhibitors in human plasma as nonesterified fatty acids and lysophospholipids" *J. Biol. Chem.,* 261:11704–11711 (1986).

Kramer et al., "Antinatriferic activity in human plasma following acute and chronic salt–loading" *Kidney International,* 12:214–219 (1977).

Lichtstein et al., "Identification of digitalis–like compounds in human cataractous lenses" *European Journal of Biochemistry,* vol. 216, pp. 261–268 (1993).

Lichtstein et al., "Effect of salt acclimation on digitalis–like compounds in the toad" *Biochem. Biophys. Acta.,* 1073:65–68 (1991a).

Lichtstein et al., "Identification of 11,13–dihydroxy–14–octadecaenoic acid as a circulating . . . " *J. Endocrinol.,* 128:71–78 (1991b).

Lichtstein et al., "Identification of a ouabain–like compound in toad skin and plasma as a bufodienolide derivative" *Life Sciences,* 38:1261–1270 (1986).

Lichtstein et al., "Evidence for the presence of 'ouabainlike' compound in human cerebrospinal fluid" *Brain Res.,* 325:13–19 (1985).

Lichtstein and Samuelov, "Endogenous 'ouabain like' activity in rat brain" *Biochem. Biophys. Res. Com.,* 96:1518–1523 (1980).

Lowry et al., "Protein measurement with the folin phenol reagent" *J. Biol. Chem.,* 36:265–275 (1951).

Meyer and Kinde, "Collection of toad venoms and chemistry of the toad venom steroids" in *Venomous Animals and Their Venoms,* vol. 2, pp. 521–522, eds. W. Bucherl and E. Buckley, NY Academic Press (1971).

Moreth et al., "Blood pressure in essential hypertension correlates with the concentration of a circulating inhibitor of the sodium pump" *Klinische Wochenschrift,* 64:239–244 (1986).

Nakano et al., "Study on the subretinal fluid report 1. refracto–metric and paper–electrophoretic study . . . " *Jap. J. Ophthalmol.,* 14:196 (1960).

Ng et al., "Ascorbia acid: an endogenous inhibitor of isolated . . . " *Biochem. Pharmacol.,* 34:2525–2530 (1985).

Russell et al., "Properties of a Na–K ATPase inhibitor in cultured lens epithelial cells" in *Vision Research,* vol. 21, pp. 37–39 (1981).

Sen and Pffifer, "Characterization of partially purified (Na+ and K+) –ATPase from porcine lens" *Biochim. Biophys. Acta.,* 693:33–34 (1982).

Tamura et al., "Isolation and characterization of a specific endogenous Na . . . " *Biochemistry,* 27:4244–4253 (1988).

Tamura et al., "Lysophosphatidylcholines containing polyunsaturated fatty acids were found as Na . . . " *Biochemistry,* 26:2797–2806 (1987).

Tamura et al., "Identification of linoleic and oleic acids as endogenous Na . . . " *J. Biol. Chem.,* 260:9672–9677 (1985).

Van Winkle et al., "The nature of the transport ATPase–digitalis complex: III. Rapid binding studies . . . " in *Archives of Biochemistry and Biophysics,* vol. 151, No. 1, pp. 85–92 (1972).

Vasdev et al., "Dehydroepiandrosterone sulfate as a digitalis like factor in plasma of healthy human adults" *Res. Commun. Chem. Path. and Pharmacol.,* 49:387–399 (1985).

Wechter and Benaksas, "Natriuretic hormones" *Prog. Drug. Res.,* 34:231–260 (1990).

19-NORBUFALIN
MW 372

*Fig-5a*

BUFALIN
MW 386

*Fig-5b*

3-HYDROXY-14(15) -EN-
19-NORBUFA-
20,22-DIENOLIDE
MW 354

*Fig-5c*

19-NORBUFALIN-
PEPTIDE CONJUGATE
MW 602

*Fig-5d*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear

( i i ) MOLECULE TYPE: peptide

( x i ) SEQUENCE DESCRIPTION: SEQ ID NO:1:

Ala  Gly  Thr
    1

DIGITALIS-LIKE COMPOUNDS

This is a Continuation-in-Part application based on U.S. Ser. No. 08/397,160 filed Apr. 10, 1995 now abandoned which is a 371 of PCT/U.S. Ser. No. 93/08393 filed Sep. 8, 1993 with a priority claimed from Israeli Application Number 103,132 filed Sep. 10, 1992.

BACKGROUND OF THE INVENTION

1. Technical Field

This application relates to the identification, isolation and characterization of endogenous digitalis-like compounds and their administration as therapeutic agents.

2. Background Art

The $Na^+,K^+$-ATPase (E.C.3.6.1.3) is an integral plasma membrane protein responsible for the maintenance of $Na^+$ and $K^+$ concentration gradients in all eukaryotic cells. Since $Na^+,K^+$-ATPase has a high-affinity receptor for digitalis steroids, it has been postulated that there are endogenous ligands for these receptors which regulate the $Na^+,K^+$-pump activity. Indeed, based on their ability to inhibit [$^3$H]-ouabain binding and $Na^+,K^+$-ATPase activity, digitalis-like compounds (DLC) have been shown to be present in the brain [Haupert, G. T., Jr. & Sancho, J. M. (1979) Proc. Natl. Acad. Sci. USA 76: 4658–4660; Lichtstein, D. & Samuelov, S. (1980) Biochem. Biophys. Res. Com. 96, 1518–1523; Akagawa, K., et al., (1984) J. Neurochem. 42: 775–780], heart [De Pover, A., et al. (1982) Biochem. Pharmacol. 31: 267–271], adrenal [Tamura, M., et al., (1988) Biochemistry 27: 4244–4253], plasma [Kramer, H. J., et al. (1977) Kidney International 12: 214–219; Gruber, K. A. et al. (1980) Nature 237: 743–745; Moreth, K., et al. (1986) Klinische Wochenschrift 64: 239–244; Dasgupta, A., et al. (1987) Biochem. Biophys. Res. Commun. 148: 623–628], CSF [Halperin, J., et al. Proc. Natl. Acad. Sci. USA 80: 6101–6104; Lichtstein, D., et al. (1985) Brain Res. 325: 13–19] and urine [Cloix, J. F. et al. (1987) Can. J. Physiol. Pharmacol. 65: 1522–1527; Goto, A., et al. (1990) Biochem. Biophys. Res. Commun. 173: 1093–1101] of mammals and in the skin [Flier, J., et al. (1980) Science 208: 503–505] and plasma [Lichtstein, D., et al. (1986) Life Sciences 38: 1261–1270] of toads.

Several substances have been proposed as the DLC, including unsaturated fatty acids [Bidard, J. N., et al. (1984) Biochim. Biphys. Acta 769: 245–252; Tamura, M., et al. (1985) J. Biol. Chem. 260: 9672–9677; Kelly, R. A., et al. (1986) J. Biol. Chem. 261: 11704–11711], hydroxy unsaturated fatty acids [Lichtstein, D., et al. (1991) J. Endocrinol. 128: 71–78,], lysophosphatidylcholines [Tamura, M., et al. (1987) Biochemistry 26: 2797–2806], dopamine [Clarkson, E. M. & De Wardner, H. E. (1985) Clinical and Experimental Hypertension Part A, A7, 673–683], dehydroepiandrosterone sulfate [Vasdev, S., et al. (1985) Res. Commun. Chem. Path. and Pharmacol. 49: 387–399], lignan [Fagoo, M., et al. (1986) Biochem. Biophys. Res. Commun. 134: 1064–1070] and ascorbic acid [Ng, Y. C., et al. (1985) Biochem. Pharmacol 34: 2525–2530]. However, none of these compounds appears to be the natural ligand of the digitalis receptor of the $Na^+,K^+$-ATPase because of their limited specificity and affinity.

Bufodienolides, which resemble the structure of the plant cardiac glycosides, have been identified in the plasma, brain and other tissues of toads [Flier, J., et al. (1980) ibid.; Lichtstein, D., et al. (1986) ibid.; Meyer, K. & Kinde, H. (1971) Collection of Toad Venoms and Chemistry of the Toad Venom Steroids. Vol. 2 p. 521–552, in Venomous Animals and their Venoms, Eds W. Bucherl & E. Buckley. New York Academic Press; Lichtstein D., et al. (1991) Biochem. Biophys. Acta. 1073: 65–68]. However, the presence of bufodienolides in mammals has not yet been demonstrated. Recently, ouabain [Hamlin, J. M., et al. (1991) Proc. Natl. Acad. Sci. USA 88: 6257–6263] and digoxin [Goto, A., et al. ibid.] have been identified in mammalian tissues but their synthesis by mammals has not been demonstrated. Numerous studies have implicated DLC in the regulation of sodium and water homeostasis and pregnancy as well as pathological states such as hypertension and renal and hepatic failure [for review see De Wardener, H. E. & Clarkson, E. M. (1985) Physiological Reviews 65: 658–759; Haber, E. & Haupert, G. T. (1987) Hypertension 9: 315–324; Wechter, W. J. & Benaksas, Prog. Drug Res. 1990, 34: 231–260].

Availability of endogenous digitalis-like compounds and the possibility of their administration as therapeutic agents may result in advantageous treatment of various pathological conditions in which their involvement is implied. Such compounds may be used as cardiotonic agents, increasing the intensity of heart muscle contractions, as vasoactive agents, elevating blood pressure and as natriuretic/diuretic agents, increasing the excretion of sodium into the urine and thus increasing urine volume. In view of the marked involvement of $Na^+,K^+$-ATPase in the central nervous system, digitalis-like compounds may also be used as neuromodulating agents.

Moreover, the levels of endogenous digitalis-like compounds in body fluids or tissues may be used for diagnosing said pathological conditions such as hypertension or kidney or hepatic failure.

In search for endogenous digitalis-like compounds, the present inventors have surprisingly found that such compounds are present in human cataractous lens nuclei.

The eye lens is an avascular tissue composed of two different cell types: fiber cells that are essentially free of intracellular organelles that make up the bulk of the lens, and a single layer of epithelial cells on the anterior surface from which the fiber cells are derived [Duncan, G. & Jacob, T. J. The Eye (Davson, H., Ed.) pp. 159–206, Academic Press, Orlando, Fla., USA (1984). The anatomy and biochemistry of the lens as well as its development were extensively studied (for review see Duncan, G. & Jacob, T. J. (1984) ibid.; Cotlier E., The Lens in: Adler's Physiology of the Eye (Moses R. A. ed) 277–303, The C. V. Mosby Company, St. Louis (1981)]. Studies of lens plasma membrane ion pumps have indicated that the lens $Na^+,K^+$-ATPase could maintain intracellular $Na^+$ and $K^+$ concentrations similar to those in other tissues [Sen P. C. & Pffifer D. R. (1982) Biochim. Biophys. Acta 693: 33–34].

Several studies raised the possibility that a $Na^+,K^+$-ATPase inhibitor is involved in cataract formation. In 1960, a strain of mice that develops lens opacity shortly after birth was described [Nakano K., et al. (1960) Jap. J. Ophthalmol. 14: 196]. Further investigation of the mechanism of the development of this hereditary cataract suggested that an apparent deficiency of $Na^+,K^+$-ATPase activity in the lens may be involved [Itawa, S. & Kinoshita, J. H. (1971) Invest. Ophthalmol. 10: 504–512]. The continuation of this research led to the isolation of a "cataracteogenic factor" from mice lenses, that inhibits $Na^+,K^+$-ATPase activity [Fukui H. N., et al. (1978) Exp. Eye. Res. 26: 1–9; Russell P., et al. (1981) Vision Res. 21: 37–39]. It was further demonstrated that the levels of this endogenous inhibitor are elevated in cataractous lens but it is also present in the normal lens [Russell, P., et al. (1981) ibid.] The study of Fukui et al. [(1978) ibid.] as well as the recent study by Kami and Sakai [Kamei, A. & Sakai, H. (1989) Jap. J. Ophthalmol. 33: 348–357] strengthen the possibility that this $Na^+,K^+$-ATPase inhibitor is a peptide. However its amino acid composition and sequence have not been determined.

BRIEF DESCRIPTION OF THE INVENTION

The invention relates to a human cataractous lens nuclei methanolic extract characterized in that it comprises substances having a molecular weight lower than 3000 daltons, inhibiting ATP hydrolysis by $Na^+,K^+$-ATPase having affinity to the ouabain binding site on the enzyme and cross-reacting with an antibody directed against digoxin.

The invention also relates to compounds of the general formula:

(I)

or of the general formula:

(II)

in which R is hydrogen, an amino acid, a di- or tripeptide or a mono-, di- or trisaccharide.

Compounds of general formula I are preferred. Preferred compounds of formula I are those in which R is a hydrogen atom.

Preferred amino acids as the R substituent are threonine, glycine and alanine. Preferred di- or tripeptides as the R substituent are peptides consisting of said three amino acid residues.

Preferred saccharide as the R substituent is mannose.

The isolation and identification of compounds of general formula I and II are described hereinafter in the Examples, which also demonstrate their digitalis-like activity.

The invention is also concerned with pharmaceutical preparations comprising as active ingredient a therapeutically effective amount of the human cataractous lens nuclei extract of the invention, optionally further comprising pharmaceutically acceptable additives, in a pharmaceutically acceptable carrier or diluent.

The invention also relates to pharmaceutical preparations comprising as active ingredient a pharmaceutically effective amount of at least one compound of formula I or formula II, and optionally further comprising pharmaceutically acceptable additives, in a pharmaceutically acceptable carrier or diluent.

Preferred preparations of Formula I comprise as active ingredient 19-norbufalin (FIG. 5A) or its conjugate (FIG. 5D) with Thr—Gly—Ala—$NH_2$ (SEQ ID No: 1). Preferred preparations of Formula II comprise as active ingredient 3-hydroxy-14(15)-en-19-norbufa-20,22-dienolide (FIG. 5C) or its conjugate with Thr—Gly—Ala—$NH_2$ (SEQ ID No: 1)

The preparations of the invention can also comprise as the active ingredient suitable mixtures of at least two compounds of formula I or at least two compounds formula II, or at least two compounds one of Formula I and one of Formula II, or other combinations thereof, are also envisaged.

The pharmaceutical preparations of the present invention may be used for the treatment of malfunctions such as cardiac arrhythmia and cardiac failure, for the induction of natriuresis and diuresis, for the constriction of smooth muscles in arterioles, causing increase in blood pressure and as neuromodulators affecting the central nervous system.

The present invention also provides methods of preventing or treating cardiac arrhythmia and cardiac failure, renal malfunction, methods for inducing natriuresis and diuresis, and for modulating activity of the central nervous system in patients in need of such treatment, by administering to the patient an amount of a pharmaceutical preparation of the present invention effective to prevent the cardiac failure, cardiac arrhythmia, renal malfunction or correct such existing pathological conditions, or induce natriuresis or diuresis, or modulate the activity of the central nervous system.

BRIEF DESCRIPTION OF THE FIGURES

FIG. 3A–B are graphs of the elution profile of DLC on high performance liquid chromatography, C-18 column. Aliquots of the partially purified material obtained from the <3000 dalton cutoff filter (see Materials and Methods) were dissolved in water and injected onto a Lichrospher RP-18 column (0.4×25 cm, 5 µm particle size) equilibrated with 80% acetonitrile and eluted with a linear 5–80% acetonitrile gradient in 60 min at a flow rate of 3 ml/min. (FIG. 3A) The line represents the absorbance at 254 nm. (FIG. 3B) The digitalis-like activity in each fraction was determined by its ability to inhibit [$^3H$]-ouabain binding (solid bars).

FIG. 4A. Negative chemical ionization mass spectrum of fraction VI; FIG. 4B. Negative chemical ionization mass spectra of commercial bufalin (Sigma Chemicals, St. Louis, Mo. U.S.A.); FIG. 4C. Positive chemical ionization mass spectra of fraction II.

FIGS. 5A–D: Postulated structures of mammalian digitalis-like compounds. FIG. 5A 19-Norbufalin; FIG. 5B Bufalin; FIG. 5C 3-hydroxy-14(15)-en-19-norbufa-20,22-dienolide; FIG. 5D 19-Norbufalin-peptide conjugate.

DETAILED DESCRIPTION OF THE INVENTION

The invention relates to a human cataractous lens nuclei methanolic extract characterized in that it comprises substances having a molecular weight lower than 3000 daltons, inhibiting ATP hydrolysis by Na$^+$,K$^+$-ATPase, having affinity to the ouabain binding site on the enzyme and cross-reacting with an antibody directed against digoxin.

Figure 1:
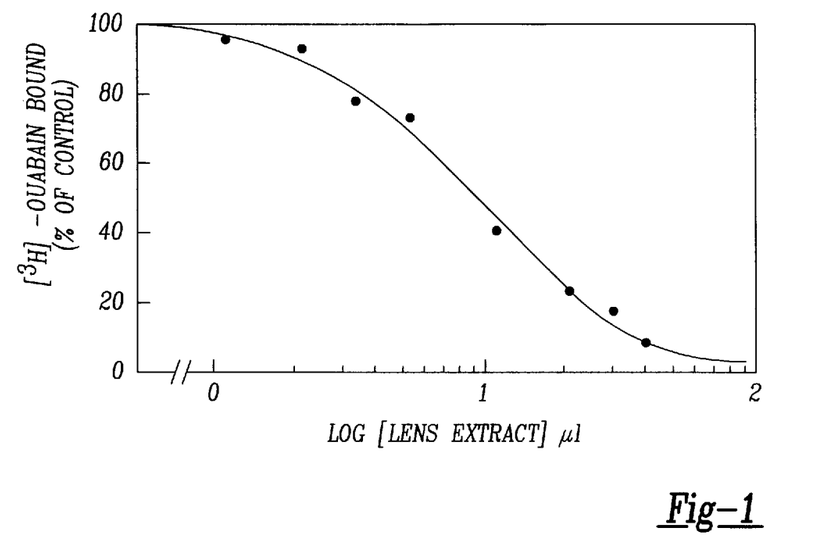
FIG. 1 is a graph of a displacement curve of [$^3H$]-ouabain binding to rat brain synaptosomes by digitalis-like compounds (DLC) partially purified from human cataractous lenses. Control [$^3H$]-ouabain binding in the absence of DLC was 15 pmol/mg protein.
Figure 2:
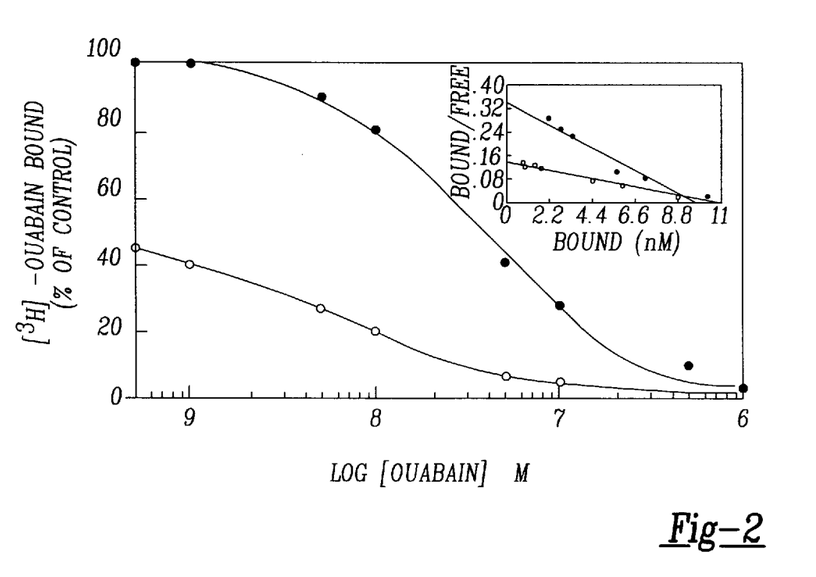
FIG. 2 is a graph of a displacement curve of [$^3H$]ouabain by unlabelled ouabain in the presence and absence of rat lens digitalis-like compounds (DLC). The binding of [$^3H$] ouabain to rat brain synaptosomes in the presence (○) and absence (●) of 40 nM (ouabain equivalents) lens DLC was performed as described in Materials and Methods. Insert is a Scatchard analysis of the displacement data.

Preparation of the human cataractous lens nuclei extract according to the invention is described in detail in the following Examples. The Examples also demonstrate that the human cataractous lens extract of the invention exhibits digitalis-like activity in that it inhibits, in a dose dependent fashion, [$^3$H]-ouabain binding to rat brain synaptosomes, it inhibits ATP hydrolysis by rat brain microsomal Na$^+$,K$^+$-ATPase and binds with an antibody directed against digoxin. The dose dependency of the inhibition of [$^3$H]-ouabain and Na$^+$,K$^+$-ATPase activity by the human cataractous lens extract of the invention is similar to the effects of known cardiac glycosides and spans two log units for complete pharmacological effect. This is shown in FIGS. 1 and 2 and TABLE 1 hereafter.

The invention also relates to compounds of the general formula:

(I)

or of the formula:

(II)

in which R is hydrogen, an amino acid, a di or tripeptide or a mono-, di- or trisaccharide.

The isolation and characterization of compounds of general formulae I and II are described hereinafter in Examples, which also demonstrate their digitalis-like activity. Most preferred compounds of formula I are 19-norbufalin (FIG. 5A) and its conjugate (FIG. 5D) with the tripeptide Thr—Gly—Ala—NH$_2$ (SEQ ID No: 1). Alternative combinations of the amino acids may also be used.

Most preferred compounds of formula II are 3-hydroxy-14(15)-en-19-norbufa-20,22-dienolide (FIG. 5C) and its conjugate with the tripeptide Thr—Gly—Ala—NH$_2$ (SEQ ID No: 1). Alternative combinations of the amino acids may also be used.

Figure 4A:
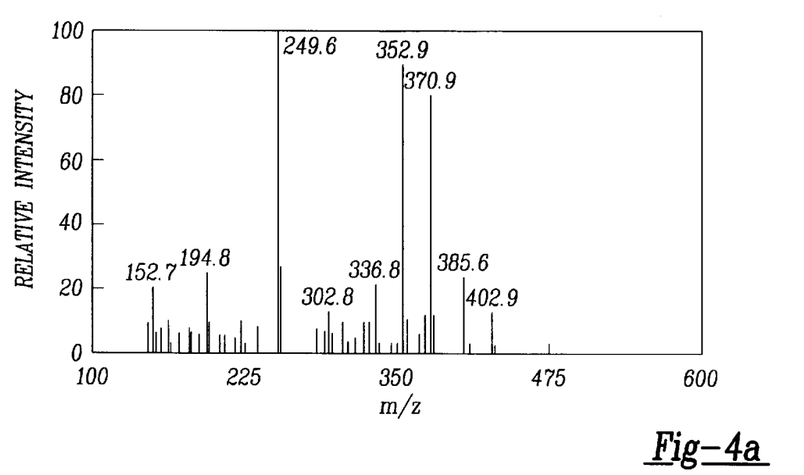
FIG. 4A–C are chemical ionization mass spectra of bufalin and purified material from human cataractous lens nuclei. Chemical ionization mass spectra were determined on Finnigan TSQ 70 mass spectrometer using isobutan as the ionization reagent as described in Materials and Methods.
Figure 4B:
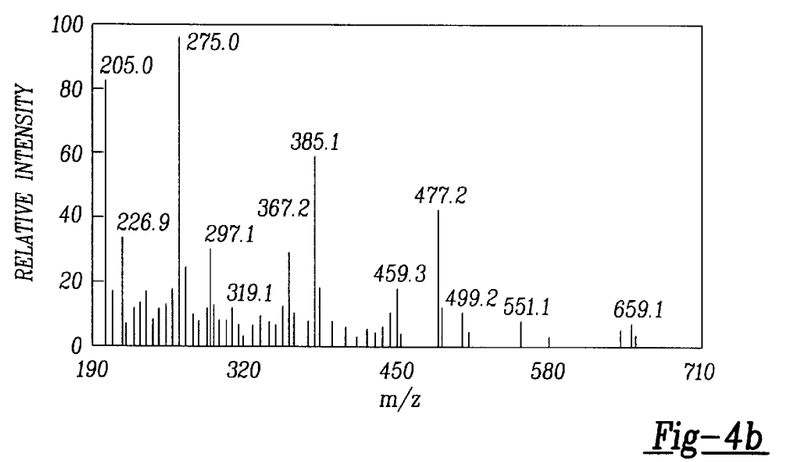
Figure 4C:
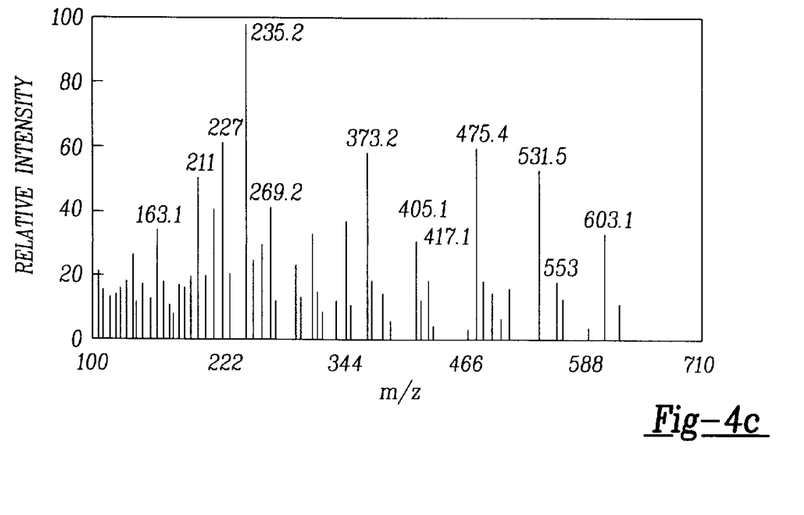

The structure of compounds of general formula I resembles the structure of some bufodienolides which were identified as normal constituents of toad skin and plasma [Flier, J., et al. (1980) ibid.; Lichtstein, D., et al. (1986) ibid.; Meyer, K. & Kinde, H. (1971) ibid.]. This is based on the following observation: (1) the mass spectrum of Fractions VI and II of the human cataractous lens nuclei extract of the present invention corresponds to the suggested dienolide structures (FIG. 4A–C); (2) the maximum UV absorbance of material in Fraction VI was 298 nm, a UV maximum characteristic of the dienolide system (TABLE 3) [Meyer, K. & Kinde, H. (1971) ibid.]; and (3) the digitalis-like activity characteristic of steroids as delineated above. The present invention implies that the synthesis of 6-membered cyclic unsaturated lactone steroids is not restricted to amphibian but is also achieved by mammalian tissues.

The invention is also concerned with pharmaceutical preparations comprising as active ingredient a therapeutically effective amount of the human cataractous lens nuclei of the invention, optionally further comprising pharmaceutically acceptable additives, in a pharmaceutically acceptable carrier or diluent.

The invention also relates to pharmaceutical preparations comprising as active ingredient a pharmaceutically effective amount of at least one compound of formula I or of formula II, optionally further comprising pharmaceutically acceptable additives, in a pharmaceutically acceptable carrier or diluent.

Preferred preparations of Formula I comprise as active ingredient 19-norbufalin (FIG. 5A) or its conjugate (FIG. 5D) with Thr—Gly—Ala—NH$_2$ (SEQ ID No: 1). Preferred preparations of Formula II comprise as active ingredient 3-hydroxy-14(15)-en-19-norbufa-20,22-dienolide (FIG. 5C) or its conjugate with Thr—Gly—Ala—NH$_2$ (SEQ ID No: 1)

Preparations can also comprise as the active ingredient suitable mixtures of at least two compounds of formula I or of formula II or of both.

The pharmaceutical preparations of the present invention may be used for the treatment of malfunctions such as cardiac arrhythmia and cardiac failure, for the induction of natriuresis and diuresis, for the constriction of smooth muscles in arterioles, causing increase in blood pressure and as neuromodulators affecting the central nervous system. The effectivity of the pharmaceutical compositions of the invention is based on the established biological effects of cardiac glycosides and bufodienolides and the resemblance thereto of the compounds of the present invention, which constitute the active ingredient of the pharmaceutical compositions according to the invention. This effectivity is also based on the ability of the compounds of the invention to inhibit Na$^+$,K$^+$-ATPase activity, as will be shown in the Examples hereafter.

The present invention also provides methods of preventing or treating cardiac and renal malfunctions, methods for inducing natriuresis and diuresis, and for modulating activity of the central nervous system in patients in need of such treatment, by administering to the patient an effective amount of a pharmaceutical preparation of the present invention effective to prevent the cardiac failure, arrythmia or the like or renal malfunction or correct such existing pathological conditions, or induce natriuresis or diuresis, or modulate the activity of the central nervous system.

The preparations according to the invention may be administered orally or parenterally in dosage unit formulations containing conventional nontoxic pharmaceutically acceptable carriers, diluents, adjuvants and vehicles as desired. The term parenteral as used herein includes subcutaneous, intravenous, intramuscular, intraarticular and intrathecal injection and infusion techniques, slow-release subcutaneous implants or targeted delivery systems such as monoclonal antibodies, vectored delivery, iontophoretic, polymer matrices, liposomes, and microspheres.

Dosage unit preparations may contain daily required amounts of the compounds of the invention or submultiples thereof to make up the desired dose. The specific therapeutically effective dose level for any particular patient will depend upon a variety of factors including the activity of the specific compound employed, the age, body weight, general health, sex, diet, time of administration, route of administration, rate of excretion, etc. The treatment generally has a length proportional to the length of the disease process and drug effectiveness.

As used herein, the term "pharmaceutically acceptable carrier" means an inert, non-toxic solid or liquid filler, diluent or encapsulating material, not reacting with the active ingredients of the invention. These carriers are known to those versed in the art. Wetting agents, emulsifiers and lubricants, as well as coloring agents, release agents, coating agents, sweetening and flavoring agents and preservatives can also be present in the preparations of the invention. The amount of active ingredient that may be combined with the carrier materials to produce a single dosage form will vary depending upon the patient treated and the particular mode of administration.

The compounds of the invention utilized in the present invention, can be administered in combination with other drugs or pharameceutically acceptable additives, consistent with good medical practice. They are administered and dosed in accordance with good medical practice taking into account the clinical condition of the individual patient, the site and method of administration, scheduling of administration, and other factors known to medical practitioners.

In a further aspect, the invention is concerned with diagnostic preparations and kits for the determination of the level of compounds of formula I or II in body fluids or tissues such as plasma, urine, CSF and lens tissue, under physiological and pathological conditions. The compounds can be detected utilizing immunohistochemical staining, ELISA, RIA, immunoblots, immunoprecipitation, and functional assays. Results of such diagnostic tests are of considerable assistance in treatment of the patient.

The compounds of formula I or II are used as antigens, to elicit formation of antibodies thereagainst for use in these assays. These antibodies are used in diagnostic preparations for the determination of the level of compounds of formula I or II in body fluids or tissues in pathological or physiological conditions, employing known immunoassay techniques.

Antibodies may be either monoclonal or polyclonal. Conveniently, the antibodies may be prepared against the compounds of the present invention and/or portions thereof may be isolated and used as the immunogen. Such compounds can be used to produce antibodies by standard antibody production technology well known to those skilled in the art as described generally in Harlow and Lane, *Antibodies: A Laboratory Manual,* Cold Spring Harbor Laboratory, Cold Spring Harbor, N.Y., 1988 and Borrebaeck, *Antibody Engineering—A Practical Guide,* W. H. Freeman and Co., 1992.

For producing polyclonal antibodies a host, such as a rabbit or goat, is immunized with the compounds of the present invention, generally with an adjuvant and, if necessary, coupled to a carrier; antibodies to the compound are collected from the sera. Further the compounds can be blocked to prevent activity in the host if necessary.

For producing monoclonal antibodies the technique involves hyperimmunization of an appropriate donor with the compounds of the present invention or portion thereof, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice,* Blackwell Scientific Publications, Oxford, 1982.) The binding of antibodies to a solid support substrate is also well known in the art. (see for a general discussion Harlow & Lane *Antibodies: A Laboratory Manual,* Cold Spring Harbor Laboratory Publications, New York, 1988 and Borrebaeck, *Antibody Engineering—A Practical Guide,* W. H. Freeman and Co., 1992) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

In general, ELISAs are the preferred immunoassays employed for determination of the level of compounds of formula I or II in body fluids and immunohistochemical staining for tissue screening. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. No. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521.

EXAMPLES

MATERIALS AND METHODS

Lenses extraction: Human cataractous lens nuclei were obtained from patients which were medication-free, undergoing cataract surgery at the Shaarey Zedek and Hadassah Hospitals in Jerusalem. The lens nuclei were immediately frozen and kept at −20° C. until used. Pooled 20–30 lens nuclei were homogenized in methanol. The homogenate was kept for 1 hour at 4° C. and the precipitate removed by centrifugation (28,500×g, 4° C). The methanol was evaporated and the residue dissolved in distilled water. The sample was centrifuged again under the same conditions and the aqueous supernatant separated and applied to Sep-pak® C-18 columns (Wators, Mass., U.S.A.). The Sep-pak® columns were washed with 10 ml water and the active material was eluted by 80% acetonitrile. The acetonitrile was evaporated and the residue was dissolved in water. The sample was applied to Centricon-3 (3,000 MW cutoff) microconcentrator tubes (Amicon Mass., U.S.A.) which were centrifuged for 3 hours at 5,000×g. The material that passed the filter (<3000 Dalton) was collected, concentrated and applied to HPLC for fractionation (see Results). The material obtained at this stage of purification is termed, in the present study, 'partially purified material'. Rat, rabbit and bovine lenses were extracted and partially purified in a manner identical with the human cataractous lenses extraction.

Assays for digitalis-like activity (FIG. 2): The digitalis-like activity of each fraction obtained in the course of the purification was determined using two independent bioassays. Inhibition of [$^3$H]-ouabain binding: The binding of [$^3$H]-ouabain to rat brain synaptosomal fractions was carried out by a conventional filtration technique as previously described [Lichtstein, D., et al. (1991) ibib.].

In brief: the reaction mixture (500 μl final volume) contained the following constituents (final concentrations): Tris-HCl (50 mM) buffer (pH 7.4), EDTA (0.4 mM), NaCl (80 mM), MgSO4 (4 mM), ATP (2 mM, Tris, vanadium-free), [$^3$H]-ouabain (32 nM, 19.5 Ci/mmol, New England Nuclear, Dreisich, Germany) and other additions as indicated. Reactions were initiated by the addition of 200 µl crude synaptosomal fraction resulting in a final protein concentration of 200 µg/reaction.

Following incubation for 1 hour at 37° C., the reactions were terminated by the addition of 3 ml cold (4° C.) Tris-HCl (50 mM, pH 7.4) and filtered over Whatman GF/B filters (Tamar Inc., Jerusalem, Israel). Filters were washed twice with 3 ml of the same Tris buffer, dried and assayed for radioactivity in a Packard liquid scintillation counter at a counting efficiency of approximately 50%. Specific binding was calculated by subtracting the binding observed in the presence of 100 µM unlabelled ouabain from that observed in the absence of unlabelled ouabain. Specific binding represented 93% of the total binding under control conditions. All samples tested for their ability to inhibit [$^3$H]-ouabain binding were analyzed previously for Na$^+$ and K$^+$ levels. In all cases K$^+$ final concentrations were too low (<10 µM) to affect the binding characteristics.

Inhibition of Na$^+$,K$^+$-ATPase activity: Na$^+$,K$^+$-ATPase activity in rat brain microsomal fraction was determined as previously described (Lichtstein, D., et al. (1991) ibid.]. Enzyme activity was measured by the calorimetric determination of inorganic phosphate after the incubation of microsomes (30 µg protein/reaction) at 37° C. in a solution (final volume 500 µl) containing (final concentrations) Tris-HCl (50 mM, pH 7.4), NaCl (100 mM), KCl (10 mM), MgCl$_2$ (4 mM) and ATP (2 mM, Tris, vanadium free). After a 10 minute preincubation, the ATP was added to initiate the reaction. Reactions were terminated by the addition of 100 µl 5% trichloroacetic acid and the precipitate was removed by centrifugation. Ouabain-insensitive ATPase activity was determined by the addition of ouabain (1 mM) to the assay mixture.

Measurement of digoxin-like immunoreactivity: Radioimmunoassay was performed with digoxin RIA kit obtained from Amersham International (Amersham, Buckinghamshire, England). Assay conditions were as recommended by the manufacturer.

High-performance liquid chromatography (HPLC): Reversed-phase HPLC were run on a Lichrospher RP-18 column (0.4×25 cm, 5 µm particle size, Merck, Darmstadt, Germany) using the Hewlett Packard HPLC pump (Model 1050) connected to computerized diode array detector (Model 1040M). The columns were pre-equilibrated with water containing 0.1% trifluoroacetic acid before sample application and developed with a linear gradient of acetonitrile of 0–80% acetonitrile containing 0.1% trifluoroacetic acid for 60 min at a flow rate of 1 ml/min. The elution of the compounds from the columns was monitored at various wavelengths using the diode array detector and each sample was measured for digitalis-like activity as described above.

Mass spectrum measurements: Mass spectra were recorded by negative and positive chemical ionization on a Finnigan TSQ 70 mass spectrometer using isobutane as the ionization reagent. The samples were inserted by direct inlet with a chemical desorption sampler. The samples were heated from 25° to 250° C. and the spectra were automatically recorded.

Na$^+$,K$^+$ and protein determinations: Na$^+$,K$^+$ were determined by atomic absorption using a Perkin-Elmer atomic absorption spectrometer (Norwalk, Conn., U.S.A.). Protein concentration was determined by the colorimetric method [Lowry, O. H., et al. (1951) J. Biol. Chem. 36: 265–275].

RESULTS

Digitalis-like activity in human cataractous lenses and normal animal lenses:

The inhibition of [$^3$H]-ouabain binding to rat brain synaptosomes by partially purified lens extract is demonstrated in FIG. 1. The dose response of this inhibition spans two log units as expected from mass-action law for ligand receptor interaction. Assuming that the compound has the same affinity to the ouabain receptor as ouabain, the levels of DLC in the lens could be estimated. In 71 different pooled lens nuclei extracts, 15±7 nmol/gr wet weight (Mean±S.E.M. ouabain equivalents) were found (the large variability in DLC levels in the cataractous lens is referred to in the following discussion).

Furthermore, the partially purified material from human cataractous lens extract inhibited, dose dependently and specifically, the ATP hydrolysis by rat brain microsomal Na$^+$,K$^+$-ATPase (Table 1). Importantly, extract concentration that caused 80% inhibition of Na$^+$,K$^+$-ATPase activity had only marginal effect on Mg$^{++}$-ATPase activity.

In Table 1 data is presented from human cataractous lens nuclei which were extracted and partially purified as described in Materials and Methods. ATPases activity were performed on rat brain microsomal membrane fraction. Values are from a single experiment conducted in triplicates.

The partially purified material from human cataractous lenses was also tested for its ability to cross react with digoxin antibody in comparison to ouabain and bufalin (Table 2). The three compounds cross reacted with the antibody resulting in a cross reactivity of 0.012, 0.045 and 0.022% for ouabain, bufalin and the lens extract, respectively. It should be pointed out that the cross reactivity calculation for the compound in the lens were done under the following assumptions: (a) that the compound has an identical affinity to ouabain in the [$^3$H]-ouabain binding assay; (b) that it has a MW of 372; and (c) that a single compound is involved.

In Table 2, the data are from digoxin radioimmunoassays which were performed using a commercially available kit. The concentration of the partially purified lens DLC was determined from its ability to inhibit [$^3$H]-ouabain binding assuming identical affinity to the ouabain receptor as ouabain and MW of 372.

In order to eliminate the possibility of contamination of the extract with cardiac glycosides or bufodienolides present in the laboratory, the extraction and purification was repeated three times in a different laboratory (different building) with identical results. In additional three experiments, water was substituted for lens extract and was taken through the extraction and purification procedures. No digitalis-like activity (inhibition of [$^3$H]-ouabain binding and Na$^+$,K$^+$-ATPase activity) was apparent.

Taken together, the effects of the partially purified cataractous lens extract on [$^3$H]-ouabain binding, Na$^+$,K$^+$-ATPase and digoxin antibody, strongly suggest the existence of DLC in this tissue.

Purification of digitalis-like compounds:

In the present study approximately 600 human cataractous lens nuclei were used. The lenses were homogenized in methanol and extracted and partially purified as described in Materials and Methods. The material obtained was redissolved in distilled water and applied to fractionation on HPLC.

Figure 3A:
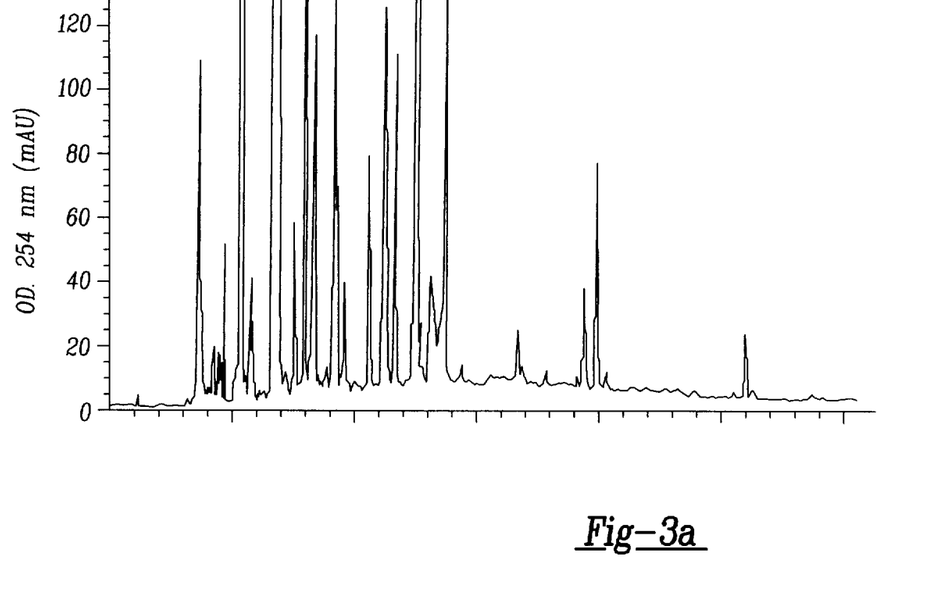
Figure 3B:
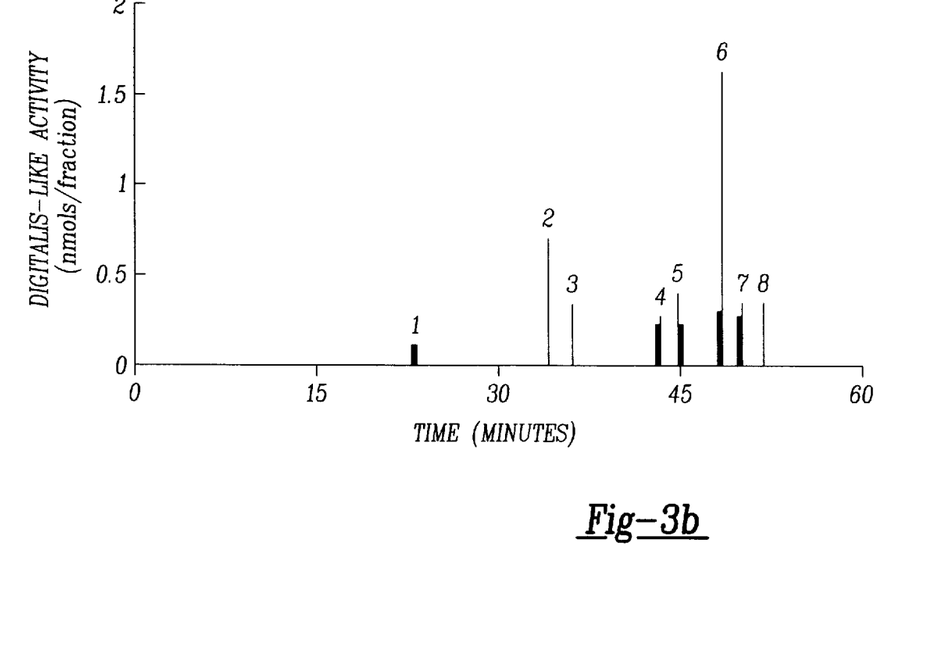

The elution profile of the samples from reverse phase C-18 column is shown in FIG. 3. The digitalis-like activity was fractionated into eight peaks of activity designated I to VIII. Each of these peaks inhibits, in a dose dependent manner, [$^3$H]-ouabain binding to rat brain synaptosomes and rat brain microsomal Na$^+$,K$^+$-ATPase activity (data not shown). Some chemical characteristics of these peaks are summarized in Table 3. Most of the digitalis-like activity was obtained in peak VI and peak II. While peak VI shows a clear maximum of UV absorbance at 298 nm, peak II shows a maximum at 289 nm (Table 3).

The maximum absorbance of each peak of activity in the chromatogram (FIG. 3 and Table 3) was determined using the diode array detector. Percent digitalis-like activity was determined by measuring the ability of each fraction to inhibit [$^3$H]-ouabain binding to rat brain synaptosomes (FIG. 3B). The reactivity of each fraction to diazomethane was measured by treating the partially purified extract with etheral solution of diazomethane prior to the fractionation on HPLC.

In order to shed light on the chemical nature of the compounds involved, an experiment was conducted in which the lens extract was treated with diazomethane prior to its separation on HPLC. The rational was that if free carboxylic acid is involved in the structure the compound will either lose its biological activity or be shifted in the chromatogram. As can be seen in Table 3, a variety of results were obtained for the different peak. Peak VII disappeared from the chromatogram, peak IV was significantly shifted and some peaks (I, II, VI, VIII) were not affected by the treatment. These results may indicate that a mixture of compounds with similar biological activity is present in the cataractous lens.

Figure 5A:
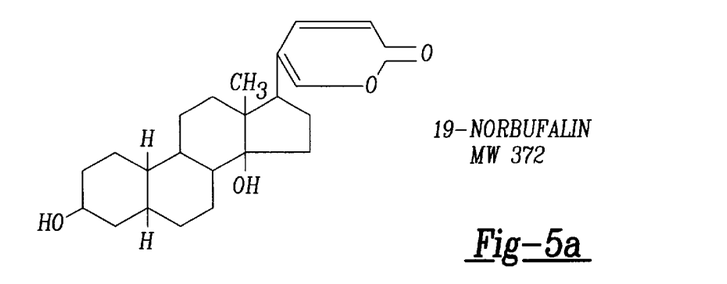
Figure 5B:
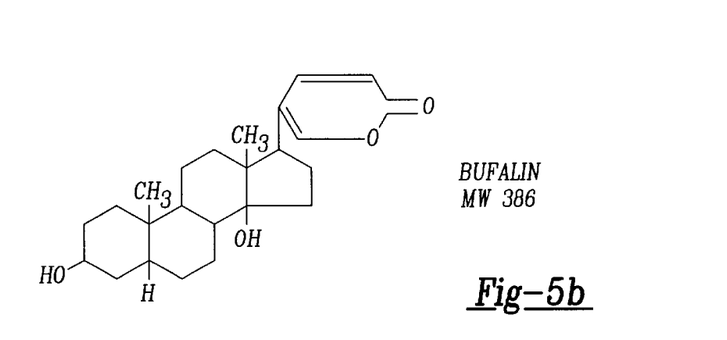
Figure 5C:
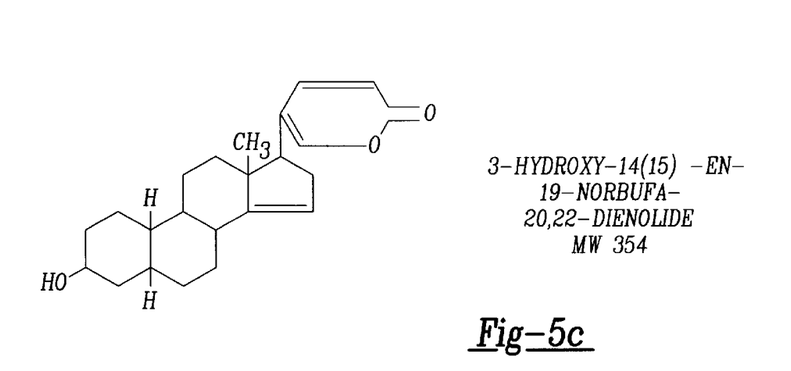
Figure 5D:
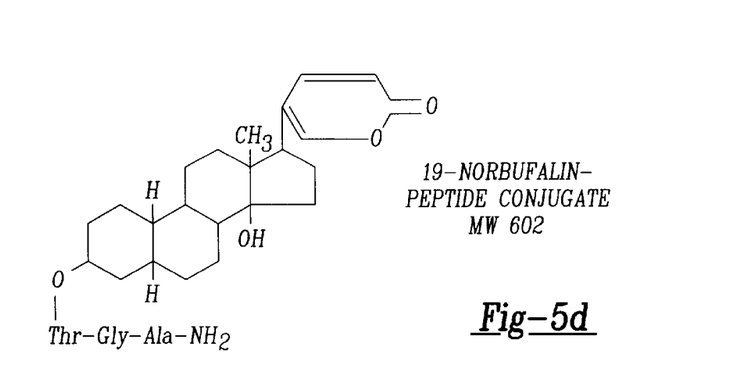

Structure Identification:

Identification of the structure of the endogenous compounds was performed on fractions VI and II. As mentioned above, fraction VI, with the retention time of 46.5–47.5 minutes, shows a UV absorbance with lambda max of 298 nm suggesting that a bufodienolide structure may be present in this fraction. The mass spectral analysis using negative chemical ionization of this fraction is shown in FIG. 4A (M-1 ions are shown). It reveals a small peak at m/z 385 and two larger peaks at m/z 371 and 353. The peak at 385 may correspond to cholesterol (MW 386) which is known to be present in the lens but may also correspond to the bufodienolide bufalin. In addition to cholesterol, two other bufodienolides, 19-norbufalin (MW 372; FIG. 5A) and its dehydrated derivative (MW 354; FIG. 5C), may be present in this fraction. The large peak at m/z 249 (FIG. 4A) is due to a sodium-glycerol cluster ion $G_2Na_3$. For comparison, the mass spectrum of bufalin (FIG. 5B), obtained also in negative chemical ionization, is shown in FIG. 4B. It shows a peak at m/z 385 corresponding to the (M—H)$^-$ ion and a peak at m/z 477 due to the bufalin-glycerine adduct, without undergoing further fragmentation. Glycerin trimer (m/z 275), tetramer (m/z 367) and sodium-glycerine cluster (m/z 205) are also present in this mass spectrum.

The mass spectrum of the more polar fraction (fraction II, retention time 33.5–34.5 min.) further supports these conclusions. The mass spectrum, measured by positive chemical ionization mode which shows mainly protonated ions (M+1 ions), is depicted in FIG. 4C. It shows peaks at m/z 373, 475, 531 and 603 au. Analysis of this mass spectrum suggests that the 19-norbufalin (MW 372; FIG. 5A) is bound in this fraction to a small peptide (Thr—Gly—Ala (SEQ ID No: 1), 373+101+57+72=603) or fragments of this peptide (373+101+58=532 and 373+102=475). The 253 peak, due to the sodium-glycerol cluster ($G_2Na_3$) is the most abundant peak in this spectrum. Due to the minute quantities of material available, it was not possible to conclude whether fraction II is a mixture of these derivatives or a homogenous compound.

Throughout this application, various publications, including U.S. patents, are referenced by citation or number. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

EFFECT OF HUMAN CATARACTOUS LENS PARTIALLY PURIFIED EXTRACT ON Na$^+$,K$^+$-ATPase ACTIVITIES

| Na$^+$,K$^+$-ATPase | | Mg$^{++}$-ATPase | |
|---|---|---|---|
| (nmolPi/mg protein/min) Lens extract (arbitrary units) | (% of control) | n(molPi/mg protein/min) | (% of control) |
| 0    45.7 | 100  | 4.7 | 100 |
| 0.5  28.6 | 63   | 4.7 | 100 |
| 1    25.7 | 56   | 3.8 | 80  |
| 2.5  19   | 41.7 | 3.8 | 80  |
| 5    17.1 | 37.5 | 3.8 | 80  |
| 10   9.5  | 20.8 | 3.8 | 80  |

TABLE 2

DIGOXIN-LIKE IMMUNOREACTIVITY IN PARTIALLY PURIFIED HUMAN CATARACTOUS LENS EXTRACT

| Compound 10 μg/ml | Digoxin-like immunoreactive material, ng/ml | Cross reactivity % |
|---|---|---|
| Digoxin | 10,000 | 100 |
| Ouabain | 1.21 | 0.012 |
| Bufalin | 4.53 | 0.045 |
| Lens Extract | 2.26 | 0.022 |

TABLE 3

CHEMCIAL FEATURES OF THE SEPARATED DLC FROM CATARACTOUS LENSES

| Fraction | Retention Time (min) | % Acetonitrile | % of Total Digitalis-like Compound | Maximum Absorbance of Purified Compound | Treatment with Diazomethane |
|---|---|---|---|---|---|
| I   | 22.5–23.5 | 23 | 4  | 248 and 298 | no shift |
| II  | 33.5–34.5 | 34 | 22 | 289         | no shift |
| III | 35–35.5   | 35 | 7  | 275         | not known |

TABLE 3-continued

CHEMCIAL FEATURES OF THE SEPARATED DLC FROM CATARACTOUS LENSES

| Fraction | Retention Time (min) | % Acetonitrile | % of Total Digitalis-like Compound | Maximum Absorbance of Purified Compound | Treatment with Diazomethane |
|---|---|---|---|---|---|
| IV | 43–44 | 43.5 | 10 | 278 | shift of 1 min. |
| V | 44–45 | 44.5 | 11 | 275 | not known |
| VI | 46.5–47.5 | 44.5 | 32 | 298 | no shift |
| VII | 48.5–49.5 | 49 | 9 | not known | disappearance |
| VIII | 50–50.5 | 50 | 5 | 296 | no shift |

What is claimed is:

1. A compound of a formula selected from the group consisting of:

and in which R is a hydrogen atom, an amino acid, a di- or tripeptide or a mono-, di- or trisaccharide.

2. Compound according to claim 1 wherein R is a hydrogen atom.

3. Compound according to claim 1 wherein said amino acid is threonine, glycine or alanine.

4. Compound according to claim 1 wherein said di- or tripeptide wherein the amino acids which form the di or tripeptide are selected from the group consisting of threonine, glycine and alanine residues.

5. Compound according to claim 4 wherein said tripeptide is Thr—Gly—Ala—$NH_2$ (SEQ ID No: 1).

6. Compound according to claim 1 wherein R is mannose.

7. Pharmaceutical preparation comprising as active ingredient at least one compound according to claim 1 and a pharmaceutically acceptable carrier or diluent.

8. Pharmaceutical preparation according to claim 7 further including pharmaceutically acceptable additives.

9. Pharmaceutical preparation according to claim 7 wherein said active ingredient is selected from the group consisting of 19-norbufalin, norbufalin conjugate with Thr—Gly—Ala—$NH_2$ (SEQ ID No: 1), 3-hydroxy-14(15)-en-19-norbufa-20,22-dienolide and norbufalin conjugate with Thr—Gly—Ala—$NH_2$ (SEQ ID No: 1).

* * * * *